(12) United States Patent
Crowley

(10) Patent No.: US 6,626,940 B2
(45) Date of Patent: Sep. 30, 2003

(54) MEDICAL DEVICE ACTIVATION SYSTEM

(75) Inventor: Robert J. Crowley, Sudbury, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/882,829

(22) Filed: Jun. 15, 2001

(65) Prior Publication Data

US 2002/0193874 A1 Dec. 19, 2002

(51) Int. Cl.[7] .................................................. A61F 2/06
(52) U.S. Cl. ...................... 623/1.42; 623/1.1; 623/912; 606/159; 606/200
(58) Field of Search ............................ 623/24, 25, 921, 623/1.42, 912; 604/31; 606/200; 607/6, 62, 120

(56) References Cited

U.S. PATENT DOCUMENTS

| | | | |
|---|---|---|---|
| 3,570,476 A | 3/1971 | Gregg | 128/24 |
| 4,187,854 A | * 2/1980 | Hepp et al. | 607/33 |
| 4,957,501 A | * 9/1990 | Lahille et al. | 128/899 |
| 5,069,664 A | 12/1991 | Guess et al. | 604/22 |
| 5,267,954 A | 12/1993 | Nita | 604/22 |
| 5,405,318 A | 4/1995 | Nita | 604/22 |
| 5,693,091 A | * 12/1997 | Larson et al. | 623/3.27 |
| 5,972,029 A | 10/1999 | Fuisz | 623/1 |
| 6,083,232 A | 7/2000 | Cox | 606/128 |

FOREIGN PATENT DOCUMENTS

| | | |
|---|---|---|
| WO | WO 98/34564 | 8/1998 |
| WO | WO 00/00252 | 1/2000 |
| WO | WO 01/07110 A2 | 2/2001 |

OTHER PUBLICATIONS

Orhan Soykan and Maura G. Donovan, "Implantable System with Drug–Eluting Cells for On–Demand Local Drug Delivery," Applic No.: 09/745,144, Pub. No.: US 2001/0000802 A1, Pub. Date: May 3, 2001.

* cited by examiner

*Primary Examiner*—Corrine McDermott
*Assistant Examiner*—William H. Matthews
(74) *Attorney, Agent, or Firm*—Westman, Champlin & Kelly, P.A.

(57) ABSTRACT

A medical device vibratory activation system is disclosed. The system includes an implantable appliance comprising a conductive material and a signal producing mechanism having a portion configured to be located relative to the implantable appliance. The signal-producing mechanism is also configured to generate a signal that interacts with the conductive material in the implantable appliance to induce a motion of the implantable appliance.

22 Claims, 6 Drawing Sheets

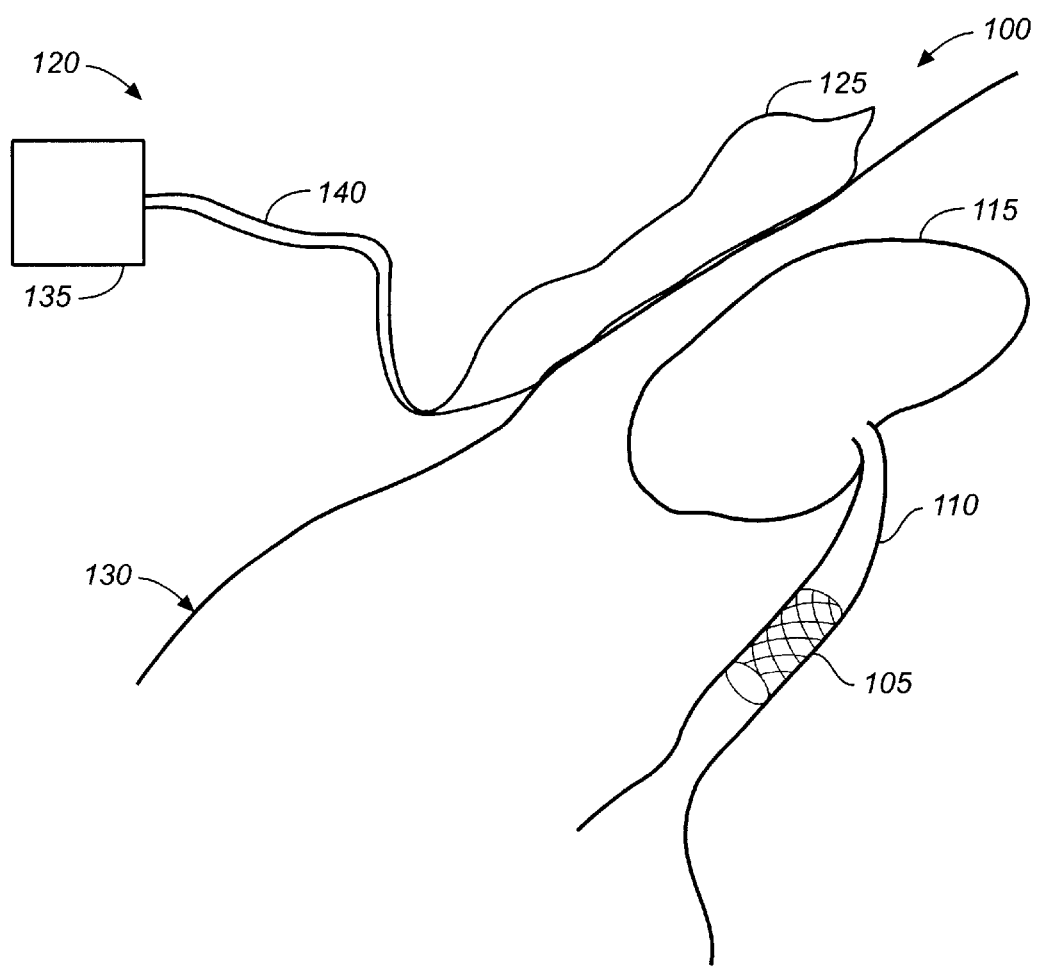
FIG._1

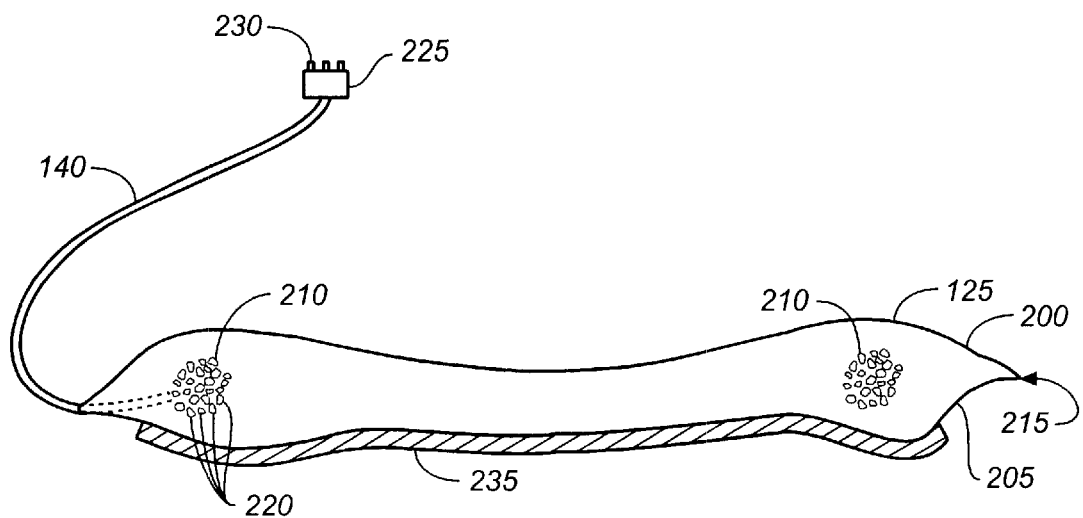
FIG._2A
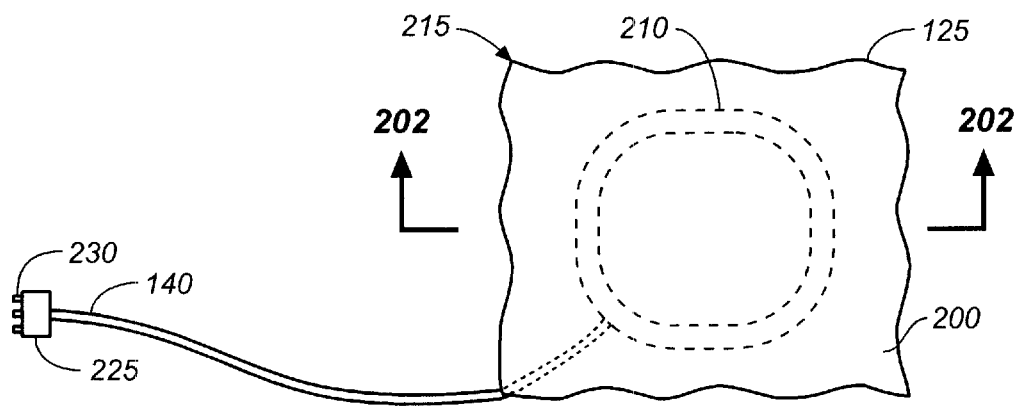
FIG._2B

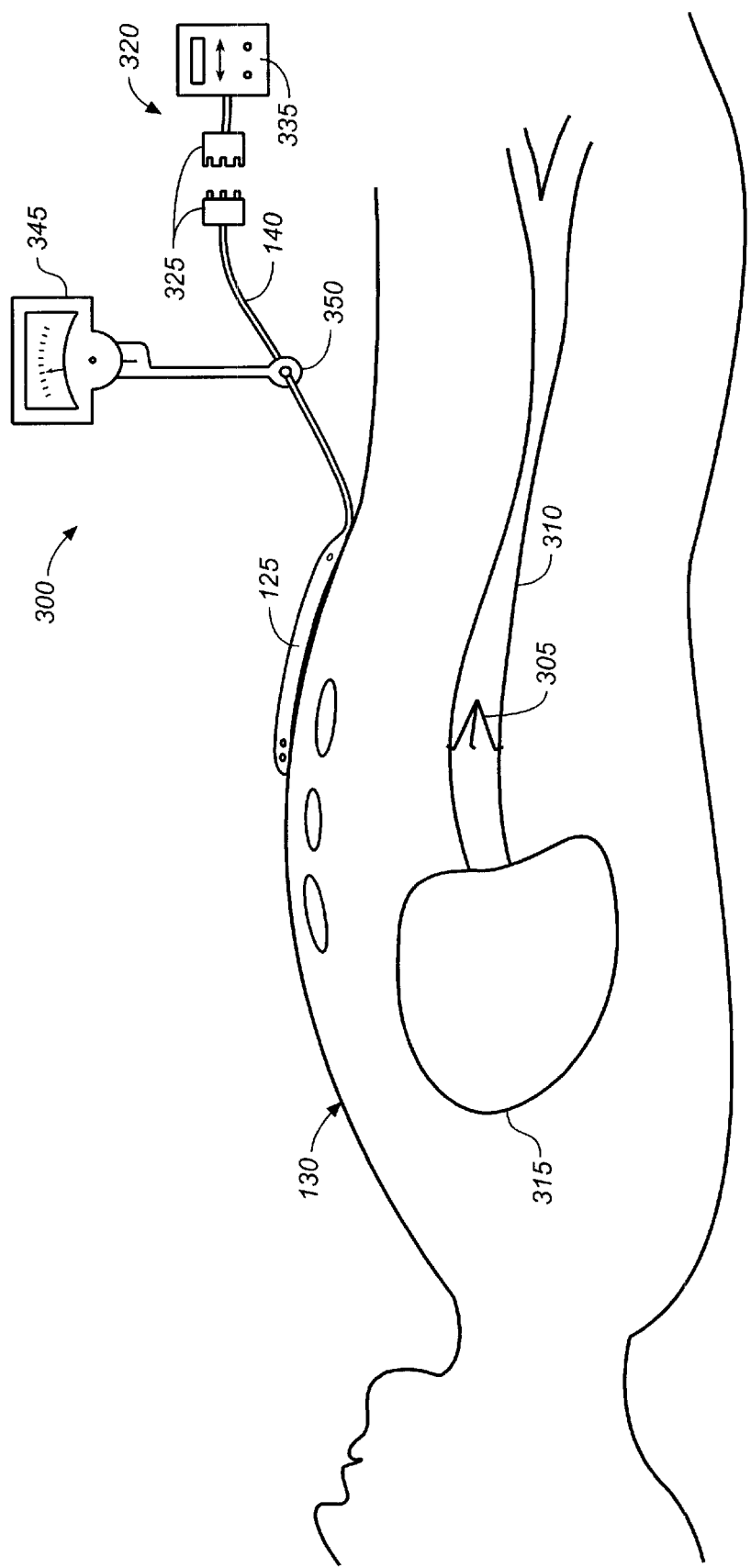
FIG._3

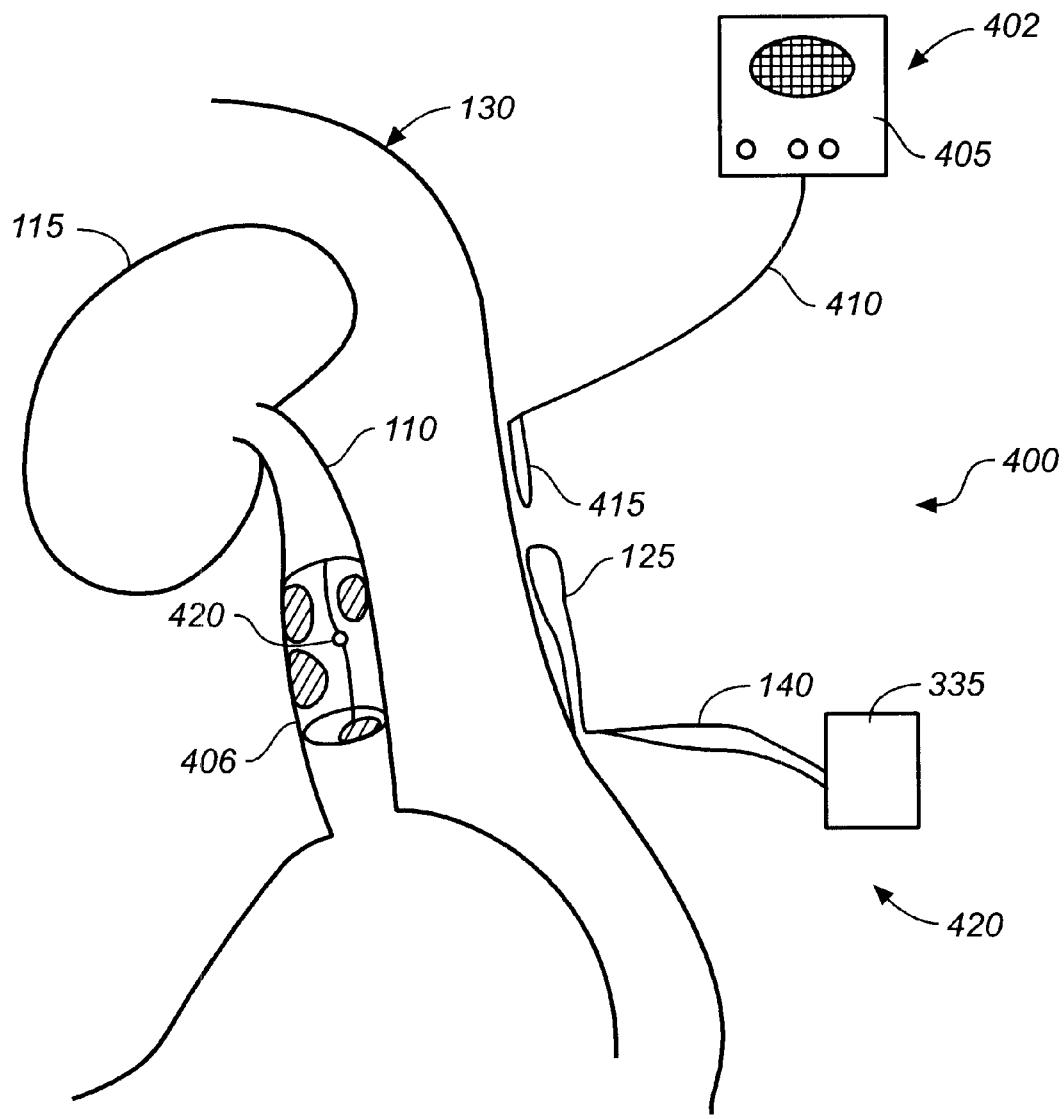
FIG._4

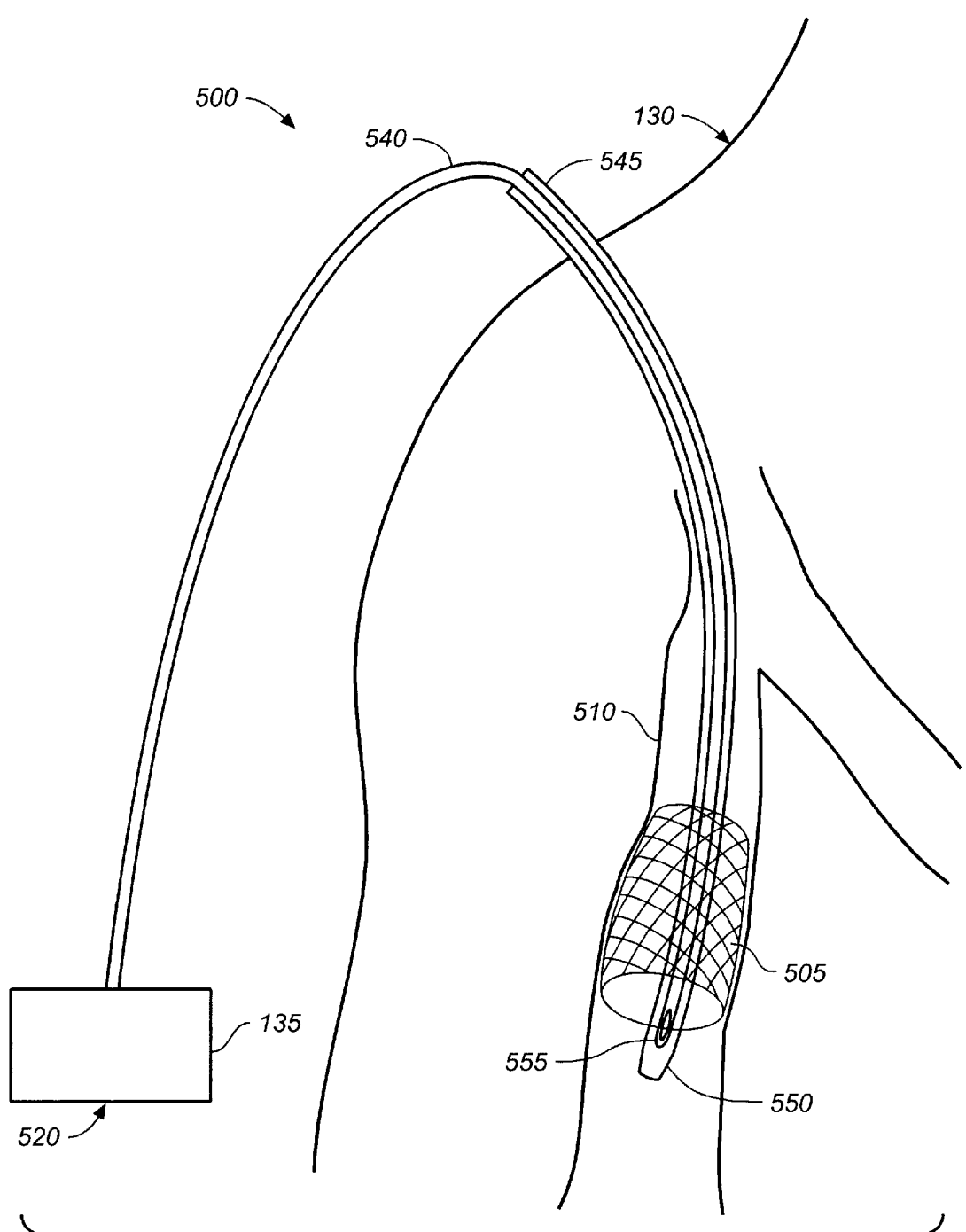
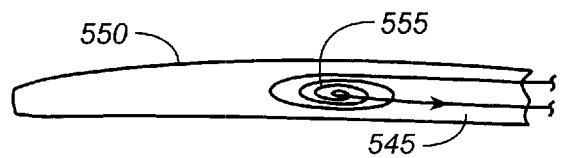

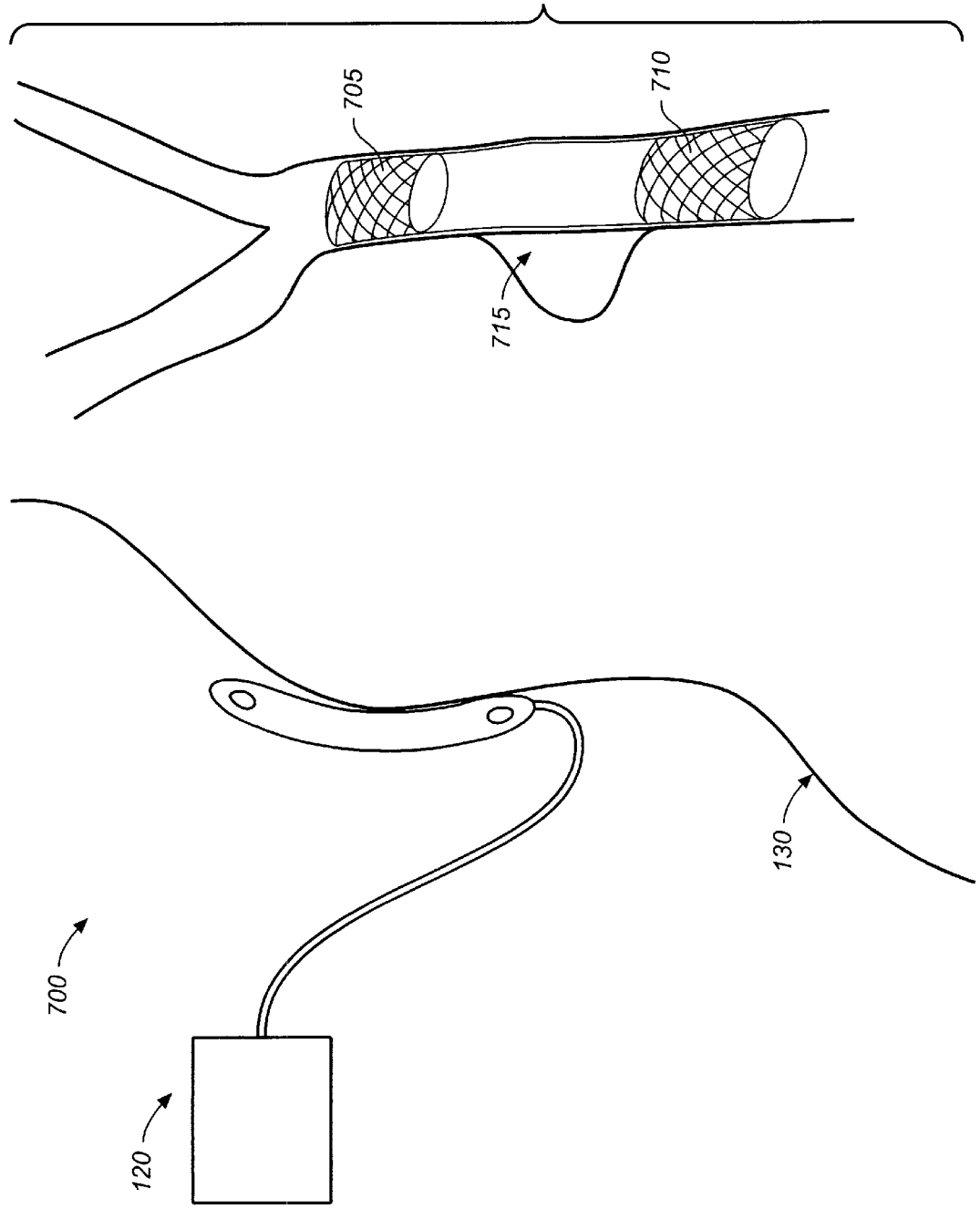

MEDICAL DEVICE ACTIVATION SYSTEM

BACKGROUND OF THE INVENTION

The present invention deals with systems and methods for actuating an implantable medical device. While the invention could be applied in the context of a variety of medical devices, the present description, for the sake of brevity, will be focused primarily on implantable stents and filters. Accordingly, the present invention deals with systems and methods for remotely actuating an implantable stent or an implantable filter.

Implanted medical devices are susceptible to becoming clogged, encrusted or otherwise compromised after placement in the various vessels, tubes, ureters and organs of the body.

Generally, the long term patency of stents in-vivo can be compromised in instances where agglomeration or encrustation is encountered. For instance, while intracoronary stenting has proven to be an arguably effective tool for coronary revascularization, the incorporated stents are susceptible to in-stent restenosis, which significantly compromises long-term effectiveness of the procedure.

Filters tend to be particularly susceptible to encrustation caused from precipitation of fluids that pass through them. This effect tends to compromise the long-term patency of filters in-vivo. Certain in-vivo filters, such as vena cava filters where blood clots tend to aggregate, are particularly vulnerable to agglomeration and encrustation.

A variety of methods have been developed and have proven to be at least partially successful in increasing the post-implantation effectiveness of stents and filters. Specialized coatings, material selection and placement techniques have been known to contribute in various ways to preventing a gradual loss of patency or effectiveness of implanted stents and filters. In addition, various acoustic ablation devices, transducers and extracorporeal acoustic generating devices have been utilized for the same purpose. These methods typically either require threading catheters into vessels, which may be undesirable, or require the use of expensive external equipment, such as shock wave lithotriptor systems, to affect and/or monitor the condition of an implanted device. Systems and methods that effectively prevent gradual losses of patentcy or effectiveness of implanted appliances, especially systems and methods that are minimally invasive and inexpensive to manufacture, are desirable.

SUMMARY OF THE INVENTION

One aspect of the present invention pertains to a medical device vibratory activation system. The system includes an implantable appliance comprising a conductive material and a signal producing mechanism having a portion configured to be located relative to the implantable appliance. The signal-producing mechanism is also configured to generate a signal that interacts with the conductive material in the implantable appliance to induce a motion of the implantable appliance.

Another aspect of the present invention pertains to a method of diagnosing a condition of an implanted medical appliance. The method comprises implanting a medical appliance that comprises a conductive material; positioning a portion of a signal-producing mechanism in a location proximate the implanted medical appliance; inducing a motion of the implanted medical appliance by utilizing the signal-producing mechanism to generate a signal capable of motion-producing interaction with the conductive material; sweeping the signal over a plurality of frequencies, wherein at least one of the frequencies is a key frequency that induces a resonant response by the implanted appliance; and identifying the key frequency.

Yet another aspect of the present invention pertains to an implanted conductive appliance electromagnetically coupled to an extracorporeal signal-producing mechanism. The extracorporeal signal-producing mechanism is configured to induce a reaction by the implanted conductive appliance.

BRIEF DESCRIPTION OF THE DRAWINGS

FIG. 1 is a schematic view of a medical device activation system.

FIG. 2A is a cross-sectional view of a coil assembly portion of the medical device activation system.

FIG. 2B is a top view of the coil assembly.

FIG. 3 is a schematic view of an embodiment of the medical device activation system, wherein the system incorporates diagnostic features.

FIG. 4 is schematic view of an embodiment of the medical device activation system, wherein the system incorporates an extracorporeal sensing mechanism.

FIG. 5 is a schematic view of an embodiment of the medical device activation system, wherein the system incorporates a transcutaneously delivered coil assembly.

FIG. 6 is a partially exposed view of the coil assembly portion of the FIG. 5 embodiment of the medical device activation system.

FIG. 7 is a schematic view of an embodiment of the medical device activation system, wherein the system is applied in the context of a stent graft.

DETAILED DESCRIPTION OF ILLUSTRATIVE EMBODIMENTS

FIG. 1 illustrates a schematic view of medical device activation system 100. The system includes a stent 105 situated within a duct or lumen 110. A vareity of simple and complex devices and methods could be utilized to deliver stent 105 to a location within lumen 110. For instance, stent 105 could be delivered utilizing any of a number of known intravascular devices, such as catheters and guide wires.

While, for the sake of brevity, the present invention will be described in the context of stents, filters, and stent grafts, the scope of the present invention should not be limited to those particular medical appliances. The present invention could just as easily be applied in the context of other medical appliances. In addition, referring to FIG. 1, duct 110 is depicted as being connected to a kidney 115. The present invention could illustratively be applied in the context of a variety of other body spaces, including but not limited to vessels, tubes, ureters, and cavities in the heart or other body lumens or organs.

In accordance with an embodiment of the present invention, stent 105, which is internally implanted within a patient's body 130, can be externally influenced by a signal-producing mechanism 120. More specifically, signal-producing mechanism 120 is configured to remotely induce motion, heating or another reaction by stent 105. In addition to stent 105 reactions, signal-producing mechanism 120 is also capable of remotely inducing similar reactions by the body tissue that surrounds stent 105 (e.g., motion of stent 105 causes a corresponding motion of tissue).

Signal-producing mechanism 120 is illustratively an extracorporeal transmitter having a coil assembly 125 electrically and operably connected to a current source 135 by connection line 140. In accordance with one embodiment, coil assembly 125 is externally placed in a location proximate to internally implanted stent 105. Coil assembly 125, specific components of which will be described in greater detail in relation to FIG. 2, illustratively includes a plurality of wire loops substantially confined within a container.

Illustratively, current source 135 includes, among other related components, an amplifier and oscillator that are configured to provide moderate amounts of alternating current across line 140 to the plurality of wire loops comprised within coil assembly 125. This communication of alternating current illustratively travels through the wire loops and, in accordance with well-known and established physical principles, enables the creation of a signal in the form of alternating magnetic or electromagnetic radiation.

In accordance with one embodiment, stent 105 comprises or is constructed of a metallic or conductive material. The signal generated by signal-producing mechanism 120, illustratively a magnetic or electromagnetic signal, interacts with and induces a current within stent 105 due to the conductive properties of material incorporated into the stent.

In accordance with one embodiment, the signal acts to induce a desired reaction by stent 105 and possibly, depending on the strength and frequency of the signal, a desired reaction by the body tissue surrounding stent 105.

Illustratively, the signal generated by signal-producing mechanism 120 can be generated at a particular frequency in order to induce a particular reaction by stent 105. At certain frequencies, for example resonant frequencies, the application of the alternating current waveform via electromagnetic or magnetic radiation is effective to induce motion or vibrations in stent 105 and possibly the body tissue that surrounds stent 105. At other frequencies, the application of electromagnetic or magnetic radiation may effectively produce heat in stent 105 and possibly in the surrounding body tissue.

In accordance with embodiments of the present invention, the above-described induced heating and/or induced motion can effectively dislodge, disrupt or otherwise alter undesired material-buildup on, around and within stent 105. The induced reactions can also reduce the proliferation of tissue cells in the vicinity of stent 105. Illustratively, either, both or other induced reactions in stent 105 can be used to effectively and desirably actuate the release of a therapeutic agent, chemical, drug or other substance that may be placed on or incorporated into stent 105.

In accordance with one embodiment, the signal produced by signal-producing mechanism 120 can be adjusted by manipulating adjustable components, such as a frequency adjustment mechanism, within or operably disposed on current source 135 (adjustable components not illustrated). For instance, the signal could be adjustable to heat stent 105 to particular desired temperatures, or the signal could be adjustable to desirably vibrate stent 105 in subsonic, sonic or ultrasonic (supersonic) ranges. Vibration, heating and other induced effects could, depending on the preferences of a system operator, be induced for a temporary or long-term duration and anywhere within a vast range of potential frequencies and levels. Illustratively, to vibrate an implanted apparatus such as stent 105, frequencies between 10 Hz and 100 KHz are effective. Other frequencies, however, could produce similar results. Higher frequencies may be used so long as the implanted appliance to be influenced is both dimensionally and electrically capable of picking up an appropriate signal and converting that signal into mechanical movement. The characteristics of a particular implanted appliance will have an impact on the required frequency.

FIG. 2A is a cross sectional view of coil assembly 125. A top view of coil assembly 125 is illustrated in FIG. 2B. The cross sectional view in FIG. 2A is illustratively taken along line 202 in FIG. 2B. Together, FIGS. 2A and 2B show components and details of coil assembly 125 that are not apparent in the FIG. 1 illustration. The same reference numerals are used in FIGS. 2A and 2B for elements that are the same or similar to those elements illustrated in previously described embodiments.

As is illustrated by FIGS. 2A and 2B, coil assembly 125 illustratively includes a first layer 200 and a second layer 205 joined at their periphery to form a container 215 that encloses a circularly wound wire coil 210. The diameter of wire coil 210 can be desirably adjusted but is illustratively roughly the size of a corresponding implanted medical apparatus or larger. Wire coil 210 illustratively includes a plurality of wire loops, several of which have been labeled as element 220 in FIG. 2A. Wire coil 210 is illustratively constructed of a metallic or conductive material (e.g., copper).

Connection line 140 is electrically and operably connected to wire coil 210. Connection line 140 is also connected to an optional electrical connector 225, which may include one or more pins 230 for facilitating an electrical and operable connection between coil assembly 125 and current source 135 (FIG. 1).

Coil assembly 125 illustratively includes an optional adhesive patch 235. Referring to FIG. 1, the skin layer of patient's body 130 provides an external mounting surface to which coil assembly 125 may be attached. Adhesive patch 235 (FIG. 2) may be used to attach coil assembly 125 to body 130. A secure attachment illustratively helps to ensure a consistent relationship between coil assembly 125 and stent 105. In accordance with one embodiment, position and orientation of coil assembly 125 may be optimized by using known ultrasound imaging systems (not illustrated) to locate the approximate position of stent 105 within patient's body 130. An optimized and consistent relationship between coil assembly 125 and stent 105 enhances the overall effectiveness of activation system 100 by ensuring a short and effective path for the signal generated by signal-producing mechanism 120 to reach stent 105 (FIG. 1).

It should be noted that signal-producing mechanism 120 is but one example of the type of signal producing mechanisms that could fit within the scope of the present invention. Other antenna-like mechanisms that produce a signal capable of reaction-inducing interaction with conductive material comprised within stent 105 are within the scope of the present invention. For example, other mechanisms that produce magnetic or electromagnetic signals, alternating or not, could be utilized without departing from the scope of the present invention.

In accordance with one embodiment of the present invention, any transducer, loudspeaker coil, diaphragm or other electromechanical transducer, piezoelectric transducer system, or metallic structure that exhibits adequate conductivity via metallic content or conductive materials in or thereon could be implemented into the present invention in a manner similar to the above-described implementation of stent 105.

FIG. 3 illustrates a schematic view of another embodiment of a medical device activation system. Medical device activation system 300 in FIG. 3 is similar to previously described system 100 (FIG. 1) but incorporates diagnostic features and a different medical appliance. As was mentioned above, the specific medical appliance incorporated into the system is not critical to the present invention. The same reference numerals are used in FIG. 3 for elements that are the same or similar to those elements illustrated in the previously described embodiments.

System 300 includes a filter 305 situated within a lumen 310. In accordance with one embodiment, filter 305 is a vena cava filter such as may be placed in a blood vessel to prevent propagation of potentially dangerous blood clots. Similar to stent 105 in FIG. 1, filter 305 could illustratively be delivered to its lumen 310 location utilizing any number of known devices and methods. Lumen 310 is depicted as being connected to a heart 315. As was mentioned above, the present invention could be applied in a variety of other body spaces.

In accordance with an embodiment of the present invention, filter 305, which is internally implanted within patient's body 130, can be externally influenced by a signal-producing mechanism 320. Similar to mechanism 120 in FIG. 1, signal-producing mechanism 320 is configured to induce motion, heating or another reaction by filter 305 and possibly a similar reaction in the body tissue surrounding the filter. Illustratively, in order to facilitate receipt of and reaction to the signal, filter 305 is constructed of a metallic or other conductive material.

System 300 illustratively includes coil assembly 125, which operates and is structured as described above in relation to other embodiments. Coil assembly 125 is electrically and operably connected to a sweep generator 335 by a connection line 140. Similar to current source 135 described above, sweep generator 335 enables the creation of a magnetic or electromagnetic signal by providing an alternating current to wires contained within coil assembly 125.

Connection line 140 illustratively includes optional electrical connectors 225, which allow sweep generator 335 to be desirably and temporarily detached from connection line 140 when system 300 is not in use or when it is desired to connect a different mechanism, such as a non-sweeping current source, to connection line 140.

In addition to being able to externally induce a physical reaction by internally implanted filter 305, signal-producing mechanism 320 includes components that enable the condition of filter 305 to be monitored (i.e., the amount and duration of undesirable build-up proximate filter 305 can be monitored). Signal-producing mechanism 320 achieves this additional function by using the described coil assembly 125 in conjunction with sweep generator 335, which is monitored by via a current probe 350 connected to an ammeter 345.

Operation of the system 300 arrangement involves utilizing sweep generator 335 to sweep the frequency (of alternating current provided to coil assembly 125) over a range of frequencies until an increase in current is noted on ammeter 345. This increase in current is illustratively the result of a resonant reaction by filter 305 in the electromagnetic field created by signal-producing mechanism 320. The resonance of filter 305 creates a "loading" effect in which transfer of energy is increased and thus detectable via ordinary means, such as ammeter 345. This frequency-sensitive response can illustratively be used as an indication of the condition of filter 305. For example, the amount or degree of thrombus, plaque, or other burden, which affects the resonant frequency of filter 305, may be predicted according to mechanical resonance rules or electrical resonance characteristics, or both. The monitoring process can be repeated as many times as desired to determine the duration of a burden and to determine the impact of various treatment techniques.

In accordance with one embodiment, optimally transferring energy to filter 305 provides an effective vibratory response by the appliance with minimum of heating effects and loss of power. This frequency-sensitive point of optimal transfer can be detected and used as an indication of the condition of filter 305. Predictions can be made according to mechanical resonance rules or electrical resonance characteristics, or both.

In accordance with one aspect of the present invention, a condition of filter 305, such as an approximate amount of accumulated undesirable material in the vicinity of filter 305, can be diagnosed using a method designed to accommodate the system described in reference to FIG. 2. The method includes implanting filter 305, which, as has been described above, illustratively comprises a metallic or conductive material. Coil assembly 125 of signal-producing mechanism 320 is externally positioned in a location proximate internally implanted filter 305. Motion of filter 305 is induced by utilizing signal-producing mechanism 320 to generate a signal capable of motion-producing interaction with the conductive material comprised within filter 305. Sweep generator 335 is utilized to sweep the signal over a plurality of frequencies, wherein at least one of the frequencies is a key frequency that induces a resonant response by filter 305. The key frequency is identified. The condition of filter 305 is determined based on the key frequency identified. Illustratively, the amount of undesirable material built up on filter 305 is determined by analyzing mechanical and electrical resonance characteristics of the filter at the key frequency.

FIG. 4 illustrates a schematic view of another embodiment of a medical device activation system, namely system 400. As has been emphasized above, the specific medical appliance and body space contexts incorporated by the systems of the present invention are not critical. FIG. 4 illustratively depicts a stent 406 situated in a duct 110 attached to a kidney 115. The same reference numerals are used in FIG. 4 for elements that are the same or similar to those elements illustrated in previously described embodiments.

System 400 includes a signal-producing mechanism 420 that includes coil assembly 125, which is operably and electrically attached to a sweep generator 335 by a connection line 140. Similar to and in accordance with previously described embodiments, sweep generator 335 is illustratively configured to communicate alternating current at various frequencies through connection line 140 to coil assembly 125, thereby enabling the creation of a signal in the form of alternating magnetic or electromagnetic radiation having a variety of frequencies.

Stent 406 comprises metallic or conductive material. Similar to previously described embodiments, stent 406 is configured to react to the signal produced by signal-producing mechanism 420.

Unlike the previously described embodiments, FIG. 4 includes a sensing mechanism 402 having a sensor 415 externally disposed relative to the internally implanted stent 406. In one embodiment, sensor 415 is a coil assembly (similar to coil assembly 125 in FIG. 2) having a plurality of wire loops connected to a connection line 410. Sensing mechanism 402 is illustratively configured to extracorporeally sense at least one active characteristic of stent 406. In accordance with one embodiment, sensing mechanism 402 is configured to detect and indicate (i.e., visually indicate) stent 406 reactions that occur in response to signals produced by signal-producing mechanism 420.

Illustrativley, sensor 415 detects resonant responses by stent 406 that occur in reaction to a resonant frequency signal produced by signal-producing mechanism 420. A receiver 405 is electrically and operably connected to sensor 415 by connection line 410. In accordance with one embodiment, receiver 405 is an oscilloscope. Receiver 405 is configured to provide an indication of information sensed by sensor 415, such as a visual indication of information pertaining to stent 406 resonant and other responses. As was previously described in relation to other embodiments, information pertaining to the condition of an implantable appliance can be determined by analyzing mechanical and electrical resonance characteristics of the appliance at particular frequencies. Accordingly, information pertaining to the condition of implanted stent 406 can illustratively be determined based on information indicated on receiver 405 and information pertaining to corresponding signal frequencies.

In accordance with one embodiment, extracorporeal sensor 415 is configured to detect radiation from stent 406. Illustratively, a collection of potentially nonlinear radiation, the effect of temporarily stored energy that radiates from stent 406 after excitation by a signal generated by signal-producing mechanism 420, radiates from stent 406 and can be detected by sensor 415. Stent 406 could illustratively be equipped with an optional nonlinear junction 420 to enhance the nonlinear radiation effects. In accordance with one embodiment, optional nonlinear junction 420 is a diode component placed upon or integral to stent 406.

A signal corresponding to sensed radiation of stent 406 is illustratively transferred from sensor 415, across connection line 410 and to receiver 405. Receiver 405, illustratively an oscilloscope, provides an indication of stent 406 resonant and other radiation reactions. Accordingly, information pertaining to the condition of implanted stent 406 can illustratively be determined based on information indicated on receiver 405 and informatoin pertaining to corresponding signal frequencies.

FIG. 5 illustrates a schematic view of another embodiment of a medical device activation system, wherein a coil assembly portion of system 500 is transcutaneously delivered rather than being extracorporeally placed. The same reference numerals are used in FIG. 5 for elements that are the same or similar to those elements illustrated in previously described embodiments.

System 500 includes a stent 505 situated within a duct 510 within body 130. Stent 505 illustratively comprises metallic or conductive material and, similar to previously described embodiments, is configured to react to a signal produced by a signal-producing mechanism 520.

Signal-producing mechanism 520 includes an intra-vascular device 545, illustratively a catheter or guide wire, that includes a distal end 550 configured to be delivered to the internal implantation site of stent 505. A coil assembly 555 is illustratively attached to or contained within the distal end 550 of intra-vascular device 545. FIG. 6 is a partially exposed illustration of distal end 550 of intra-vascular device 545 and more clearly shows an embodiment where coil assembly 555 is disposed within the device 545.

In accordance with one embodiment, coil assembly 555 is electrically and operably attached to a distal end of connection line 540 (FIG. 5). A length of connection line 540 is either connected to or comprised within intra-vascular device 545. Current source 135 is electrically and operably connected to a proximal end of connection line 540 so as to enable a communication of current, illustratively alternating current, from current source 135, through connection line 540 and to coil assembly 555. In accordance with one embodiment, current source 135 is a frequency sweep generator as described above in previously described embodiments. In accordance with another embodiment, the current communicated from current source is non-alternating, sunusoidal, pulsating or a single burst of current.

In accordance with one embodiment, coil assembly 555 is illustratively configured to receive alternating current and respond with the creation of a signal in the form of magnetic or electromagnetic radiation that, similar to previously described embodiments, induces a vibrating or other reaction by coil 505. In accordance with another embodiment, mechanical vibrations induced in stent 505 are illustratively optimized to positively affect and reduce proliferation of cells in the vicinity of stent 505. Illustratively, a useful range of frequencies to reduce proliferation includes but is not limited to 10 KHz to 10 MHz. The shape and mass of the stent, its magnetic properties and other factors affect the resonant frequency of the stent and, as in the previously described embodiments, it may be desirable to sweep and achieve resonance.

FIG. 7 illustrates a schematic view of another embodiment of a medical device activation system, namely system 700. System 700 includes a signal-producing mechansim 120 that illustratively operates as described above in relation to FIG. 1. System 700 also includes stent graft 715, which includes stents 705 and 710, both comprising metallic or other conductive material and graft section 711 coupled to stents 706 and 710. Stents 705 and 710 are configured to react to a signal produced by signal-producing mechanism 120 in a manner that is similar to the reaction of stent 105 described in relation to FIG. 1. Accordingly, stent graft 715, as a whole, is illustratively also capable of such reaction. For instance, when stents 705 and 710 vibrate in response to a received signal, stent graft 715, as a whole, will also vibrate.

It should be noted that each of the above described system embodiments are advantageous because they include light weight components that can be manufactured at low cost. In addition, in accordance with embodiments of the present invention, the signal-producing mechanisms described with reference to the different system embodiments could illustratively be battery operated and portable. The implantable device can be a single material or an alloy, compound or other combination of materials.

In accordance with an embodiment of the present invention, induction of the above-described implanted device reactions, including a vibratory reaction, can be accomplished using an acoustic signal generator that generates an acoustic signal that subsequently interacts with the implanted devices. In accordance with embodiments, the acoustic signal generator could be extracorporeal deliverable or could includes a portion that is deliverable on a distal end of a catheter, guide wire or similar delivery device. Illustratively, the previously illustrated embodiments of the present invention could be similarly carried out with substitution of an acoustic signal generator and a corresponding acoustic signal.

Although the present invention has been described with reference to preferred embodiments, workers skilled in the art will recognize that changes may be made in form and detail without departing from the spirit and scope of the invention.

What is claimed is:

1. A medical device vibratory activation system, comprising:
   an implantable appliance comprising a conductive material;
   a signal-producing mechanism having a portion configured to be located relative to the implantable appliance, the signal-producing mechanism also being configured to generate an alternating signal that interacts with the conductive material in the implantable appliance to induce a vibrating motion of the implantable appliance;
   a sweep generator operably coupled to the signal producing mechanism and configured to sweep the signal over a plurality of frequencies; and
   an ammeter operably coupled to the signal-producing mechanism and configured to sense a current increase when the sweep generator generates a key frequency that induces a resonant response by the implantable appliance, wherein the key frequency is an indication of a condition of the implantable appliance.

2. The system of claim 1, wherein the implantable appliance is a metallic stent.

3. The system of claim 1, wherein the implantable appliance is a metallic filter.

4. The system of claim 1, wherein the implantable appliance is a stent graft.

5. The system of claim 1, wherein the signal-producing mechanism is an extracorporeal transmitter that produces the alternating signal.

6. The system of claim 5, wherein the extracorporeal transmitter includes an amplifier and an oscillator that are configured to provide an alternating current to a coiled loop of wire, thereby enabling creation of the alternating signal in the form of an alternating electromagnetic radiation.

7. The system of claim 1, wherein:
   the signal-producing mechanism is an extracorporeal coil comprising a plurality of wire loops substantially confined within a container; and
   the alternating signal is an electromagnetic field generated in response to a current being applied to the plurality of wire loops.

8. The system of claim 7, further comprising an adhesive strip attached to the container and adapted to facilitate an attachment of the container to a patient.

9. The system of claim 1, further comprising a therapeutic agent incorporated with the implantable appliance, the therapeutic agent being operable in response to the alternating signal.

10. The system of claim 9, wherein the therapeutic agent is a drug that is released in response to the alternating signal.

11. The system of claim 9, wherein an operation of the therapeutic agent is heat sensitive and the operation depends on a change in temperature induced by the alternating signal.

12. The system of claim 9, wherein an operation of the therapeutic agent is motion sensitive and the operation depends on the motion of the implantable device induced by the signal-producing mechanism.

13. The system of claim 1, wherein the signal-producing mechanism is battery operated.

14. The system of claim 1, wherein the signal-producing mechanism comprises a current source operably connected to a coil assembly that is configured to be transcutaneously delivered to an internal location proximate the implantable appliance after it has been implanted.

15. The system of claim 14, wherein at least one connection line connects the current source to the coil assembly.

16. The system of claim 14, wherein the coil assembly is coupled to an intra-vascular device.

17. The system of claim 16, wherein the coil assembly is coupled to a catheter.

18. The system of claim 16, wherein the coil assembly is coupled to a guide wire.

19. A medical device comprising:
    an implantable conductive appliance; and
    an extracorporeal signal-producing mechanism that includes a plurality of wire loops substantially confined within a container, the extracorporeal signal-producing mechanism being electromagnetically coupled to the implantable conductive appliance and configured to interact with a conductive material and induce a motion reaction by the conductive material; and
    an oscillator and an ammeter operably connected to the extracorporeal signal-producing mechanism and configured to indicate an amount and a duration of a build-up of undesirable material on the implantable conductive appliance.

20. The medical device of claim 19, further comprising a therapeutic agent coupled to the implantable conductive appliance and actuatable in response to the motion reaction induced by the extracorporeal signal-producing mechanism.

21. The medical device of claim 19, further comprising a therapeutic agent coupled to the implantable conductive appliance and actuatable in response to a heating of the implanted conductive appliance that occurs subsequent the motion reaction.

22. A medical device comprising:
    an implantable conductive appliance;
    an extracorporeal signal-producing mechanism that includes a coiled loop of wire, the extracorporeal signal-producing mechanism being electromagnetically coupled to the implantable conductive appliance and configured to provide an alternating current to the coiled loop of wire to induce a motion reaction by the implantable conductive appliance; and
    an oscillator and an ammeter operably connected to the extracorporeal signal-producing mechanism and configured to indicate an amount and a duration of a build-up of undesirable material on the implantable conductive appliance.

* * * * *